US00PP20201P2

(12) United States Plant Patent
Klemm

(10) Patent No.: US PP20,201 P2
(45) Date of Patent: Aug. 4, 2009

(54) ***CALIBRACHOA* PLANT NAMED 'KLECA07162'**

(50) Latin Name: *Calibrachoa*
Varietal Denomination: KLECA07162

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/082,031

(22) Filed: Apr. 7, 2008

(51) Int. Cl.
*A01H 5/00* (2006.01)

(52) U.S. Cl. ..... Plt./413

(58) Field of Classification Search ..... Plt./263, Plt./413

See application file for complete search history.

*Primary Examiner*—Susan B McCormick Ewoldt
(74) *Attorney, Agent, or Firm*—Jondle & Associates, P.C.

(57) ABSTRACT

A new *Calibrachoa* plant particularly distinguished by double flowers, dark-blue flowers and hardy outdoor performance is disclosed.

1 Drawing Sheet

Genus and species: *Calibrachoa* hybrid.
Variety denomination: 'KLECA07162'.

BACKGROUND OF THE NEW PLANT

The present invention comprises a new and distinct cultivar of *Calibrachoa,* botanically known as *Calibrachoa* hybrid, and hereinafter referred to by the cultivar name 'KLECA07162'. The new cultivar originated from a hybridization made in summer of 2005 in Stuttgart, Germany. The female parent was the dark-violet-flowered proprietary *Calibrachoa* plant 'CA 05 0590' (unpatented), while the male parent was the dark violet-flowered proprietary *Calibrachoa* plant 'CA 05 0629' (unpatented).

The new cultivar was first propagated in May 2006 in Stuttgart, Germany and has been asexually reproduced by vegetative cuttings and in vitro propagation in Stuttgart, Germany for more than thirty five generations. The present invention has been found to retain its distinctive characteristics through successive asexual propagations.

Plant Breeder's Rights for this cultivar were applied for in Canada on Apr. 5, 2007 and in Switzerland on Jul. 6, 2007. 'KLEC A07162' has not been made publicly available more than one year prior to filing of this application.

SUMMARY OF THE INVENTION

The following are the most outstanding and distinguishing characteristics of this new cultivar when grown under normal horticultural practices in a greenhouse in Stuttgart, Germany.

1. Dark-blue double flower; and
2. Hardy outdoor performance.

DESCRIPTION OF THE PHOTOGRAPH

This new *Calibrachoa* plant is illustrated by the accompanying photograph which shows mature flowers, buds, and foliage of the plant; the colors shown are as true as can be reasonably obtained by conventional photographic procedures. The photograph is of a five-month-old *Calibrachoa* plant, grown in a greenhouse in Stuttgart, Germany, between January and May 2007.

DESCRIPTION OF THE NEW CULTIVAR

The following detailed descriptions set forth the distinctive characteristics of 'KLECA07162'. The data which defines these characteristics were collected from asexual reproductions carried out in Stuttgart, Germany. The plant history was taken on five-month-old plants which were planted as rooted cuttings in 11-cm pots between January and May 2007 and then grown in a greenhouse. The plants had one terminal pinch one week after potting. Color readings were taken under natural light. Color references are primarily to the R.H.S. Colour Chart of The Royal Horticultural Society of London (R.H.S.) (2001).

DETAILED BOTANICAL DESCRIPTION OF THE NEW PLANT

Classification:
- *Family.*—Solanaceae.
- *Botanical.*—*Calibrachoa* sp.
- *Common.*—*Calibrachoa*.

Parents:
- *Female.*—Dark-violet-flowered proprietary *Calibrachoa* plant 'CA 05 0590' (unpatented).
- *Male.*—Dark-violet-flowered proprietary *Calibrachoa* plant 'CA 05 0629' (unpatented).

Growth:
- *Form.*—Flat.
- *Habit.*—Trailing.
- *Height* (*measured from the top of the soil*).—6 cm.
- *Width* (*horizontal plant diameter*).—17 cm.
- *Time to produce a finished flowering plant.*—13 weeks.
- *Outdoor plant performance.*—Hardy.
- *Time to initiate and develop roots.*—18 days.
- *Root description.*—Moderate density, freely branching, white, thin roots.

Stems:
- *Length of basal branches.*—8 cm.
- *Internode length.*—0.7 cm to 1.6 cm.
- *Diameter of branches* (*from midpoint*).—2 cm to 6 cm.
- *Stem color.*—RHS 145A.
- *Texture.*—Smooth.
- *Anthocyanin.*—Absent.

*Pedicel.*—Color: RHS 144B. Length: 1.5 cm. Diameter: 0.2 cm. Texture: Smooth.

Leaves:

*Arrangement.*—Alternate.

*Size.*—Length: 1 cm to 3 cm. Width: 0.5 cm to 1.5 cm.

*Shape.*—Lanceolate to broad elliptic.

*Apex.*—Broadly acute.

*Base.*—Attenuate.

*Margin.*—Entire.

*Color* (*both immature and mature*).—Upper surface: RHS 137A. Lower surface: RHS 137C.

*Texture* (*both surfaces*).—Smooth.

*Venation.*—Pinnate.

*Venation color* (*both surfaces*).—RHS 144A.

*Petioles.*—Absent.

Flower bud:

*Shape.*—Irregular to oblong.

*Size.*—Length: 2 cm. Diameter: 0.8 cm.

*Color at tight bud.*—RHS 154C.

Inflorescence:

*Blooming habit.*—Continuous flowering during summertime.

*Inflorescene type.*—Double flowering.

*Floret type.*—Double flower (similar to carnation).

*Lastingness of individual blooms on the plant.*—7 days.

*Fragrance.*—Absent.

Flowers:

*Immature flower.*—Diameter: Horizontal: 2.6 cm. Vertical: 1.9 cm. Color: Upper surface: RHS 83A Lower surface: RHS 86C.

*Mature flower.*—Diameter: Horizontal: 2.8 cm. Vertical: 2.1 cm. Color: Upper surface: RHS 83B. Lower surface: RHS 86D.

*Corolla tube.*—Color inside: RHS 83B. Color outside: RHS 86D. Tube length: 0.5 cm. Outside texture: Smooth.

*Petals.*—Apex: Rounded to emarginate. Base: Fused into the corolla tube. Margin: Entire. Waviness of petals: Weak. Lobation: Weak. Texture (both surfaces): Smooth.

*Sepals.*—Calyx (form): Rosette. Shape: Lanceolate to elliptic. Apex: Acute. Base: Fused. Margin: Entire. Length: 1.2 cm. Width: 0.3 cm. Color: Upper surface: RHS 138A. Lower surface: RHS 138B. Texture (both surfaces): Smooth.

Reproductive organs:

*Stamens.*—Number: Ranges from none to 3. Filament color: RHS 154A. Filament length: 0.4 cm. Filament diameter: 0.1 cm. Pollen color: RHS 11A. Pollen quantity: Sparse.

*Pistils.*—Number: Ranges from none to 1. Length: 0.3 cm. Diameter: 0.2 cm. Stigma color: RHS 149A. Style color: RHS 149A.

Fruit and seed set: No seed set observed

Disease and insect resistance: No particular resistance or susceptibility has been observed.

COMPARISON WITH PARENTAL AND COMMERCIAL CULTIVARS

'KLECA07162' differs from the female parent 'CA 05 0590' (unpatented) by having dark blue flowers, while 'CA 05 0590' has dark violet flowers. 'KLECA07162' has double flowers, while 'CA 05 0590' has semi-double flowers. Additionally, 'KLECA07162' averages about 8 petals per flower, while 'CA 05 0590' averages about 6 petals per flower, with 1 to 2 petaloids.

'KLECA07162' differs from the male parent 'CA 05 0629' (unpatented) by having dark blue flowers, while 'CA 05 0629' has dark violet flowers. 'KLECA07162' has double flowers, while 'CA 05 0629' has single flowers. Additionally, 'KLECA07162' averages 8 petals per flower, while 'CA 05 0629' has 5 petals per flower.

'KLECA07162' differs from the commercial cultivar 'MF Dark Blue', also known as 'KLEC02070' (unpatented), in that 'KLECA07162' averages 8 petals per flower, while 'MF Dark Blue' has 5 petals per flower. Additionally, 'KLECA07162' has double flowers, while 'MF Dark Blue' has single flowers.

I claim:

1. A new and distinct cultivar of *Calibrachoa* plant as shown and described herein.

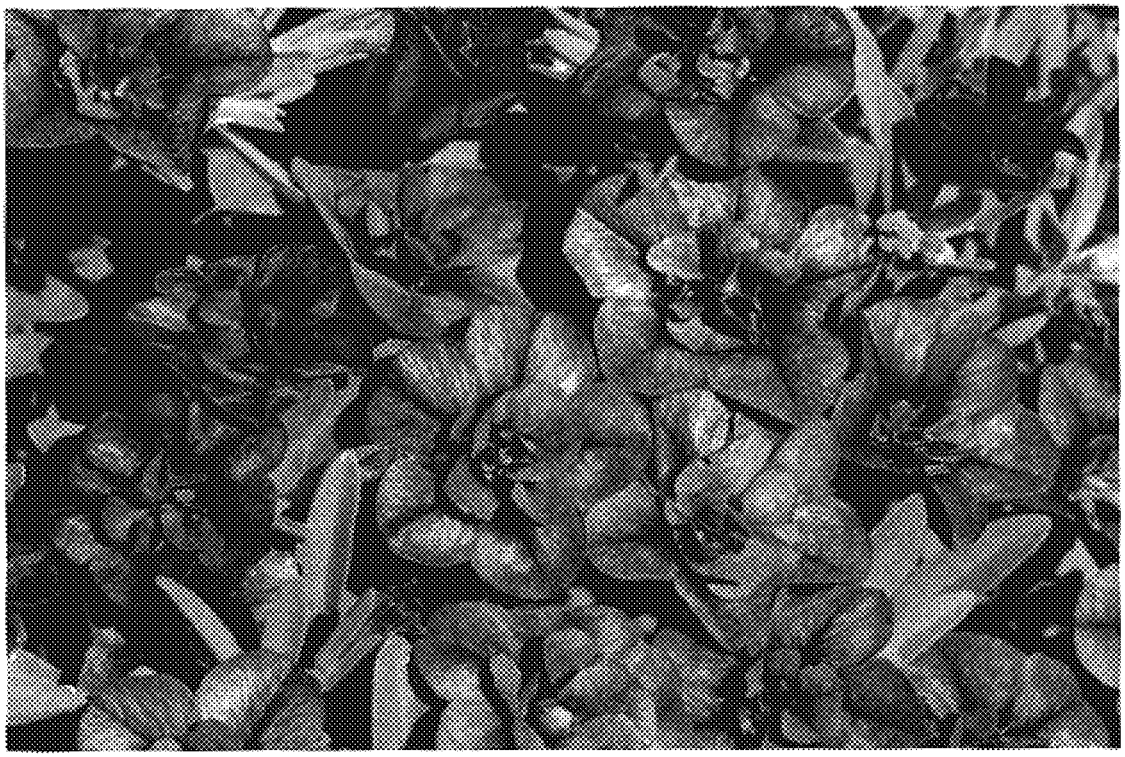

* * * * *